United States Patent [19]
Tolles

[11] 4,431,262
[45] Feb. 14, 1984

[54] CONFORMABLE OPTICAL COUPLERS

[76] Inventor: Walter E. Tolles, Lee Highway, Fairfield, Va. 24435

[21] Appl. No.: 309,035

[22] Filed: Oct. 6, 1981

[51] Int. Cl.³ .............................................. G02B 5/14
[52] U.S. Cl. ............................ 350/96.15; 350/96.20; 350/96.21
[58] Field of Search ............... 350/96.15, 96.20, 96.21, 350/164, 165; 356/240, 244

[56] References Cited

U.S. PATENT DOCUMENTS

| | | | |
|---|---|---|---|
| 3,455,625 | 7/1969 | Brumley et al. | 350/96.22 |
| 3,922,063 | 11/1975 | Marrone | 350/96.15 |
| 4,182,545 | 1/1980 | Greer | 350/96.20 |
| 4,221,461 | 9/1980 | Bair | 350/96.20 |
| 4,384,761 | 5/1983 | Brady et al. | 350/96.20 |

FOREIGN PATENT DOCUMENTS

| | | | |
|---|---|---|---|
| 2034344 | 1/1972 | Fed. Rep. of Germany | 350/96.15 |
| 53-40583 | 4/1978 | Japan | 356/240 |
| 55-9535 | 1/1980 | Japan | 350/96.21 |
| 55-50144 | 4/1980 | Japan | 356/240 |

OTHER PUBLICATIONS

Uberbacher, IBM Tech. Disc. Bull., vol. 18, No. 2, Jul. 1975, "Fiber Optic Illuminated Switch", p. 483.
Rashleigh, Applied Optics, vol. 19, No. 14, 15 Jul. 1980, "Beam-to-Fiber Coupling with Low Standing Wave Ratio", pp. 2453-2456.
Witte et al., Review of Scientific Instruments, vol. 42, No. 9, Sep. 1971, "A Novel Light Coupling Method for Fibers", pp. 1374-1375.

Primary Examiner—John D. Lee
Assistant Examiner—Frank González
Attorney, Agent, or Firm—B. P. Fishburne, Jr.

[57] ABSTRACT

To reduce substantially the level of background light which will limit the sensitivity of any photometric measurements and to avoid using optical cements and greases and their inconveniences, optical components as employed in photometric measuring systems are coupled by an optically clear compliant member which is forced into conforming contact with two opposing optical elements. The invention finds application in photometers and densitometers, spectrophotometers, fluorometers and nephelometers. The invention may also be employed in lieu of the usual immersion oil of a high power microscope.

4 Claims, 6 Drawing Figures

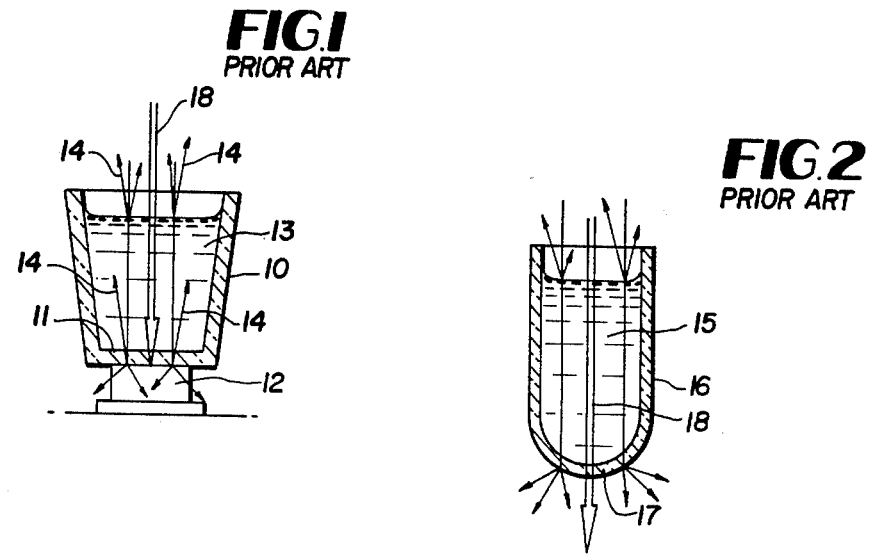
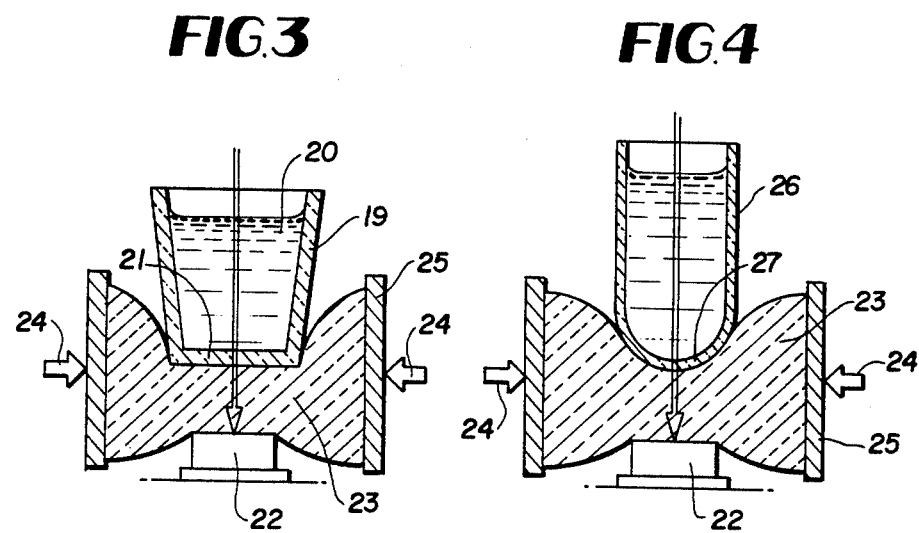
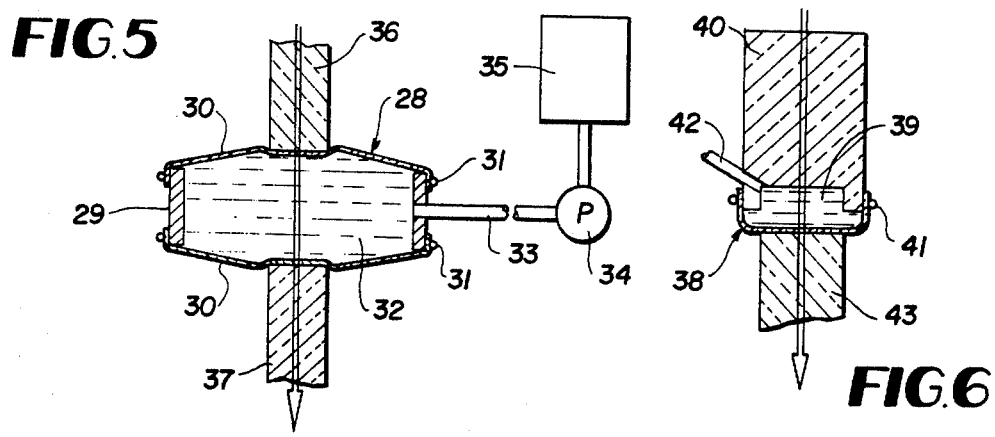

CONFORMABLE OPTICAL COUPLERS

BACKGROUND OF THE INVENTION

The problem of minimizing the level of background light which will limit the sensitivity of any photometric measurements has commonly been dealt with in the prior art by using optical cement to join optical elements permanently or by using an optical grease of a near-matching index of refraction. However, these expedients are somewhat awkward, tend to be messy, dirt-catching and are difficult to control.

Where it is desired to measure some property of a liquid or a particle suspended in a liquid which is contained in a tube or cuvette of cylindrical side wall or spherically curved bottom, these curved surfaces can be neutralized by immersion of the tube in a fluid of matching refractive index. Here again, the awkwardness of working with optical fluids is encountered, along with their tendency to become contaminated and the requirement for cleaning and replacement.

The objective of the invention, therefore, is to deal with reflected, refracted and scattered background light in optical measuring systems in a wholly different manner which does not require the use of optical cements or optical greases or fluid immersion of specimen containers and the like. In accordance with the invention, the level of background light is minimized through the use of a conformable optical coupler between opposing rigid optical elements, whether in the form of specimen containers, light detectors, light pipes or lenses. More particularly, a compliant or conformable coupling member with a refractive index in the range of 1.45 to 1.55 is interposed between spaced opposing optical elements, and through the application of forces to the coupling member and/or to the opposing optical elements, the compliant coupler is forced into intimate contact with the surfaces of the optical elements and conforms to the configurations of their surfaces. The material forming the conformable optical coupler, such as silicone rubber, is stable, transmits at least the visible spectrum, is readily castable and washable. Other suitable conformable materials may be employed.

The use of the conformable optical coupler in accordance with the invention substantially eliminates the above-noted problems of the prior art.

Other objects and advantages of the invention will become apparent during the course of the following detailed description.

BRIEF DESCRIPTION OF THE DRAWINGS

FIG. 1 is a partly schematic cross-sectional view showing an optical specimen container and associated elements in the prior art.

FIG. 2 is a cross-sectional view taken through another type of specimen container in the prior art.

FIGS. 3 and 4 are cross-sectional views showing the use of conformable optical couplers according to the invention in connection with opposing optical specimen containers and detector elements.

FIG. 5 is a cross-sectional view showing another embodiment of the conformable optical coupler according to the invention.

FIG. 6 is a cross-sectional view showing a modification of the embodiment of the invention shown in FIG. 5.

DETAILED DESCRIPTION

Referring to the drawings in detail wherein like numerals designate like parts, FIGS. 1 and 2 are intended to illustrate the problem of background light created by reflection, refraction and scattering in photometric measuring systems. More particularly, in FIG. 1, a glass specimen container 10 having a flat bottom wall 11 is shown with the bottom wall in abutment with an optical detector element 12. A liquid specimen 13 is held in the container 10. Undesirable background light which will limit the sensitivity of any photometric measurements consists of reflected light 14 at the liquid surface and at the interfacing of the container 10 and detector 12. Refractive light and scattered light also contribute to the level of the background light.

In FIG. 2, a liquid optical specimen 15 is held in a container 16 having a spherically curved bottom wall 17. Again, reflected, refracted and scattered light is involved in the total background light which detracts from the purity of the central light beam 18. As stated previously, some of the light background problem can be neutralized by immersion of the tube or container 16 in a fluid having a matching refractive index which is an awkward procedure.

In accordance with the invention, FIG. 3, a container 19 for a liquid specimen 20 having a flat bottom wall 21 is positioned in coaxial spaced relationship with a detector element 22. A conformable optical coupler 23 in the form of a disc or other body of optically clear transmitting compliant material is intervened with the flat bottom wall 21 and the opposing surface of the detector element 22. Forces 24 are brought to bear on the compliant or conformable coupler 23 acting through a marginal rigid frame or ring 25 which confines the coupler. Alternately, the container 19 and/or detector 22 can be moved axially to force the compliant coupler 23 into conforming intimate contact with their opposing faces.

The conformable optical coupler 23 has a refractive index in the neighborhood of 1.45 to 1.55. Suitably, a silicone elastomer of the type manufactured and sold by General Electric Co. or Dow Corning can be used, as well as other water clear conformable elastomers. This material transmits light in the visible spectrum, is castable and washable.

The compliant optical coupler 23, when compressed between the elements 21 and 22, eliminates substantially the background light due to reflection, refraction and scattering at least at the bottom face of the wall 21 and top face of the detector 22. The need for optical cement or grease is entirely eliminated. When pressure on the coupler 23 is relieved, it is readily separable from the opposing elements 21 and 22 and hence there is no need for optical elements being permanently joined as by cement. Further, it permits the rapid sampling of a multiplicity of specimen wells as in an automated system.

FIG. 4 depicts the utility of the dry optical coupler 23 with a liquid specimen container 26 having a spherically curved bottom wall 27, as in FIG. 2. The optical refractive difficulties inherent in the curved wall are effectively neutralized in FIG. 4 by the conformable optical coupler without the necessity for immersion of the specimen container in a liquid of matching refractive index.

FIG. 5 of the drawings shows another embodiment of the invention wherein the optical coupler 28 comprises a rigid ring 29 spanned and covered on both open ends by optically clear flexible membranes 30 suitably clamped to the ring at 31. The discoid space 32 between the two membranes 30 is filled with a clear fluid having a matching index of refraction in the range of 1.45 to 1.55. The clear fluid is supplied to the space 32 through a conduit 33 connected with a pump 34 which receives the fluid from a suitable reservoir 35.

When pressure is applied to the fluid in the space 32, the membranes 30 are expanded into conforming engagement with spaced opposing optical components 36 and 37, to be coupled, such as two light pipe elements or one such element and an optical specimen container of the types shown in FIGS. 3 and 4. Thus, a very convenient optical coupler is provided utilizing a pressurized fluid instead of the mechanical forces on the optical elastomer shown in FIGS. 3 and 4. The same advantages over the prior art prevail.

FIG. 6 shows a variant of the embodiment in FIG. 5 wherein a single membrane dry optical coupler 38 spans and covers a chamber 39 at one end of a rigid optical light pipe element 40 and is secured thereto at 41. The chamber 39 receives pressurized optical fluid through a conduit 42 in a system similar to that shown in FIG. 5. The pressurized fluid in chamber 39 expands the membrane 38 into intimate surface conforming contact with the second optical element 43 of a measuring system or the like. The described advantages over the known prior art are present in all forms of the invention. The need for optical greases is eliminated, as is the need for permanently assembling optical components with optical cement. The numerous advantages of the invention will now be understood by those skilled in the art.

It is to be understood that the forms of the invention herewith shown and described are to be taken as preferred examples of the same, and that various changes in the shape, size and arrangement of parts may be resorted to, without departing from the spirit of the invention or scope of the subjoined claims.

I claim:

1. A conformable optical coupler for spaced optical elements in an optical measuring system or the like, said coupler comprising a clear light transmitting compliant body portion interposed between said elements and having a predetermined compatible index of refraction, means to force the opposite faces of said compliant body portion into firm conforming contact with said elements to establish an optical path through the elements with minimized background light caused by reflection, refraction and scattering, said compliant body portion comprising means defining a chamber for a light transmitting pressurized fluid, and a single light transmitting flexible membrane spanning one side of said chamber and being forced by the pressurized fluid into conforming contact with an optical element.

2. A conformable optical coupler for spaced optical elements in an optical measuring system or the like, said coupler comprising a clear light transmitting compliant body portion interposed between said elements and having a predetermined compatible index of refraction, means to force the opposite faces of said compliant body portion into firm conforming contact with said elements to establish an optical path through the elements with minimized background light caused by reflection, refraction and scattering, said compliant body portion comprising means defining a chamber for a light transmitting pressurized fluid, and light transmitting flexible membranes spanning and covering opposite sides of said chamber and being forced by said fluid into conforming contact with said spaced optical elements.

3. A conformable optical coupler for spaced optical elements in an optical measuring system or the like, said coupler comprising a clear light transmitting compliant body portion interposed between said elements and having a predetermined compatible index of refraction, means to force the opposite faces of said compliant body portion into firm conforming contact with said elements to establish an optical path through the elements with minimized background light caused by reflection, refraction and scattering, and the compliant body portion comprising a light transmitting flexible membrane, and fluid pressure means to force the membrane into conforming contact with an optical element.

4. A conformable optical coupler as defined in claim 3, and said fluid pressure means comprising a pressurized chamber having its interior in communication with the flexible membrane, and pumping means exteriorly of the chamber to deliver pressurized light transmitting fluid thereto on one side of the membrane.

* * * * *